(12) United States Patent
Govari et al.

(10) Patent No.: US 11,826,529 B2
(45) Date of Patent: Nov. 28, 2023

(54) BALLOON CATHETER ASSISTED BY PULLING A PULLER-WIRE

(71) Applicant: Biosense Webster (Israel) Ltd., Yokneam (IL)

(72) Inventors: Assaf Govari, Haifa (IL); Christopher Thomas Beeckler, Brea, CA (US); Kevin Justin Herrera, West Covina, CA (US); Joseph Thomas Keyes, Sierra Madre, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 270 days.

(21) Appl. No.: 17/064,424

(22) Filed: Oct. 6, 2020

(65) Prior Publication Data

US 2021/0016067 A1 Jan. 21, 2021

Related U.S. Application Data

(63) Continuation of application No. 15/870,375, filed on Jan. 12, 2018, now Pat. No. 10,806,911.

(51) Int. Cl.
*A61M 25/10* (2013.01)
*A61M 25/00* (2006.01)
(Continued)

(52) U.S. Cl.
CPC .... *A61M 25/1025* (2013.01); *A61M 25/0023* (2013.01); *A61M 25/1006* (2013.01);
(Continued)

(58) Field of Classification Search
CPC .......... A61M 25/1025; A61M 25/1006; A61M 25/1034; A61M 25/0023; A61M 25/1018;
(Continued)

(56) References Cited

U.S. PATENT DOCUMENTS

| 5,338,301 A | * | 8/1994 | Diaz | A61M 25/104 |
| | | | | 604/103.1 |
| 5,383,923 A | | 1/1995 | Webster, Jr. | |

(Continued)

FOREIGN PATENT DOCUMENTS

| CN | 102159277 A | 8/2011 |
| CN | 204864251 U | 12/2015 |

(Continued)

OTHER PUBLICATIONS

International Search Report & Written Opinion dated May 8, 2019, from corresponding International Appl. No. PCT/IB2019/050129.

(Continued)

*Primary Examiner* — Julian W Woo
(74) *Attorney, Agent, or Firm* — Troutman Pepper Hamilton Sanders LLP

(57) ABSTRACT

A medical instrument includes a shaft, a distal-end assembly and a puller-wire. The shaft is configured for insertion into a body of a patient. The distal-end assembly, which is coupled to the shaft, includes a telescopic assembly, configured to elongate so as to collapse the distal-end assembly, and to compress so as to expand the distal-end assembly. The distal-end assembly further includes an elastic element, coupled to self-elongate and thus elongate the telescopic assembly. The distal-end assembly also includes an inflatable balloon, which is coupled to the telescopic assembly and is configured to collapse by the telescopic assembly elongating, and to expand by the telescopic assembly compressing. The puller-wire runs through the shaft and is connected to a distal end of the telescopic assembly, and is configured, when pulled, to compress the telescopic assembly.

7 Claims, 3 Drawing Sheets

(51) Int. Cl.
  *A61M 25/01* (2006.01)
  *A61B 18/00* (2006.01)
  *A61B 5/00* (2006.01)
  *A61B 18/14* (2006.01)

(52) U.S. Cl.
  CPC ....... *A61M 25/1034* (2013.01); *A61B 5/6853* (2013.01); *A61B 18/1492* (2013.01); *A61B 2018/00285* (2013.01); *A61B 2018/00351* (2013.01); *A61B 2018/00577* (2013.01); *A61M 25/0147* (2013.01); *A61M 25/104* (2013.01); *A61M 25/1018* (2013.01); *A61M 2025/0175* (2013.01); *A61M 2025/1068* (2013.01); *A61M 2025/1081* (2013.01)

(58) Field of Classification Search
  CPC .. A61M 2025/1068; A61M 2025/0175; A61M 2025/1081; A61M 25/104; A61M 25/0147; A61B 2018/00285; A61B 2018/00577; A61B 2018/00351; A61B 18/1492; A61B 5/6853
  See application file for complete search history.

(56) References Cited

U.S. PATENT DOCUMENTS

| | | | |
|---|---|---|---|
| 6,780,183 B2 | 8/2004 | Jimenez, Jr. et al. | |
| 7,931,616 B2 | 4/2011 | Selkee | |
| 8,790,300 B2* | 7/2014 | Tun | A61M 25/10 604/101.02 |
| 8,827,952 B2* | 9/2014 | Subramaniam | A61M 25/10 604/99.01 |
| 2004/0092868 A1 | 5/2004 | Murray, III | |
| 2005/0038506 A1 | 2/2005 | Webler et al. | |
| 2012/0143130 A1 | 6/2012 | Subramaniam et al. | |

FOREIGN PATENT DOCUMENTS

| | | | | |
|---|---|---|---|---|
| EP | 1634541 A1 | 3/2006 | | |
| EP | 2334365 B1 | 10/2016 | | |
| JP | H0663149 A | 3/1994 | | |
| WO | 2015044313 A1 | 4/2015 | | |
| WO | WO-2015069089 A1 * | 5/2015 | ........ A61M 25/0082 |

OTHER PUBLICATIONS

International Preliminary Report on Patentability dated Jul. 14, 2020, from corresponding International Appl. No. PCT/IB2019/050129.
First Search Report dated Dec. 28, 2021 from Corresponding Chinese Appl. No. 201980008096.7.
English translation of First Office Action dated Jan. 13, 2022, from corresponding Chinese Appl. No. 201980008096.7.
Supplementary Search Report dated Sep. 27, 2022 from Corresponding Chinese Appl. No. 201980008096.7.
English translation of Second Office Action dated Oct. 8, 2022, from corresponding Chinese Appl. No. 201980008096.7.
Notice of Reasons for Refusal dated Feb. 7, 2023, from corresponding Japanese Appl. No. 2020-538685.
Third Office Action dated Feb. 13, 2023, from Corresponding Chinese Appl. No. 201980008096.7.

* cited by examiner

BALLOON CATHETER ASSISTED BY PULLING A PULLER-WIRE

PRIORITY

This continuation application claims the benefits of priority under 35 USC 120 to prior filed patent application Ser. No. 15/870,375 filed on Jan. 12, 2018, now allowed, which is hereby incorporated by reference into this application.

BACKGROUND OF THE INVENTION

Various catheters employ different kinds of mechanisms for maneuvering the catheter distal end. For example, U.S. Patent Application Publication 2004/0092868 describes a catheter to be used without a guidewire. The catheter includes a support wire shaft formed of metal, a balloon mounted on a distal portion of the catheter, and an inflation shaft for inflating the balloon, wherein a core wire may be interchangeably inserted into the support wire shaft when the catheter is within a human body to change the stiffness and improve control thereof.

As another example, U.S. Patent Application Publication 2005/0038506 describes a medical device for treating a defective heart valve. The medical device comprises a distal anchoring member for disposing in a blood vessel, a proximal anchoring member for disposing in or at an entrance of the blood vessel, and a telescoping assembly coupling at a first end to the distal anchoring member and at a second end to the proximal anchoring member. The telescoping assembly is deployable into the blood vessel. The telescoping assembly reduces a distance between the distal anchoring member and the proximal anchoring member, wherein the telescoping assembly comprises of at least two members capable of sliding into each other giving the telescoping assembly adjustable lengths.

U.S. Pat. No. 6,780,183 describes a circumferential ablation catheter having a moveable tube that extends through a lumen of an inner support member and through the catheter body. The moveable tube is longitudinally moveable relative to the inner support member and catheter body and has a distal end that extends beyond the distal end of the inner support member. An inflatable balloon is provided generally in surrounding relation to the circumferential ablation element. The inflatable balloon has a proximal end attached, directly or indirectly, to the distal end of the catheter body and a distal end attached, directly or indirectly, to a portion of the moveable tube that extends beyond the distal end of the inner support member. Longitudinal movement of the moveable tube relative to the catheter body and inner support member causes movement of the distal end of the balloon relative to the proximal end of the balloon to thereby change the length and shape of the expanded balloon. First and second off centered puller-wires are provided for deflection of the catheter body.

U.S. Pat. No. 5,383,923 describes a steerable catheter, which is adapted to be inserted into a body lumen. The catheter comprises a symmetrical cylindrical control handle, an elongate tubular catheter body, and a flexible catheter tip having a lumen offset from the axis of the catheter tip. The control handle comprises a housing having a piston chamber at its distal end. A piston is mounted in the piston chamber and is afforded lengthwise movement. The proximal end of the catheter body is fixedly attached to the distal end of the piston. A puller-wire made of nickel-titanium alloy having shape memory is attached to the housing and extends through the piston, through and coaxial with the catheter body and into the offset lumen of the catheter tip where it is attached to the wall of the catheter tip. Lengthwise movement of the piston relative to the housing results in deflection of the catheter tip.

U.S. Pat. No. 7,931,616 describes a deflectable catheter whose puller member connections are accomplished with minimal, if any, surface deformation which could otherwise accelerate breakage under tension. The catheter includes a molded member that encases an end of a puller member to enable connection of the end to a fixed or movable structure in the control handle without significant surface deformation in the puller member. The molded member is of a thermoplastic material that encases a preformed end of the puller member, which may be a puller-wire or a high modulus fiber material. The molded member may be configured as desired, for example, as a screw that is fastened to a structure in the control handle. Alternatively, the preformed end of the puller member, for example, a puller-wire, can be directly connected to and jointly encased in the molded member with another preformed end of a second puller member, for example, a high modulus fiber material. Such a connected puller member whose distal portion is the puller-wire and whose proximal portion is the high modulus fiber material can be well suited for control handle that employs pulleys for increased throw capacity.

SUMMARY OF THE INVENTION

An embodiment of the present invention provides a catheter including a shaft, a distal-end assembly and a puller-wire. The shaft is configured for insertion into a body of a patient. The distal-end assembly, which is coupled to the shaft, includes a telescopic assembly, configured to elongate so as to collapse the distal-end assembly, and to compress so as to expand the distal-end assembly. The distal-end assembly further includes an elastic element, coupled to self-elongate and thus elongate the telescopic assembly. The distal-end assembly also includes an inflatable balloon, which is coupled to the telescopic assembly and is configured to collapse by the telescopic assembly elongating, and to expand by the telescopic assembly compressing. The puller-wire runs through the shaft and is connected to a distal end of the telescopic assembly, and is configured, when pulled, to compress the telescopic assembly.

In some embodiments, the inflatable balloon includes a distal end connected to a distal section of the telescopic assembly, and a proximal end connected to a proximal section of the telescopic assembly. In some embodiments, the elastic element includes one or more springs. In an embodiment, the elastic element includes one or more elastic splines. In another embodiment, the medical instrument further includes a handle, which is located outside the body and is configured to pull the puller-wire.

There is additionally provided, in accordance with an embodiment of the present invention, a method, including inserting into a body of a patient a medical instrument, which includes a distal-end assembly coupled to a shaft. The distal-end assembly includes (i) a telescopic assembly configured to elongate so as to collapse the distal-end assembly, and to compress so as to expand the distal-end assembly, (ii) an elastic element coupled to self-elongate and thus elongate the telescopic assembly and (iii) an inflatable balloon, which is coupled to the telescopic assembly and is configured to collapse by the telescopic assembly elongating, and to expand by the telescopic assembly compressing. The method further includes compressing the telescopic assembly by pulling a puller-wire, which runs through the shaft and is connected to a distal end of the telescopic assembly.

There is also provided, in accordance with an embodiment of the present invention, a method, including fitting at a distal end of a shaft a distal-end assembly, which includes a telescopic assembly, configured to elongate so as to collapse the distal-end assembly, and to compress so as to expand the distal-end assembly, an elastic element, coupled to self-elongate and thus elongate the telescopic assembly, and wherein the distal-end assembly further includes an inflatable balloon, which is coupled to the telescopic assembly and is configured to collapse by the telescopic assembly elongating, and to expand by the telescopic assembly compressing. The method further includes running a puller-wire through the shaft and connecting the puller-wire to a distal end of the telescopic assembly such that pulling the puller-wire compresses the telescopic assembly.

The present invention will be more fully understood from the following detailed description of the embodiments thereof, taken together with the drawings in which:

DETAILED DESCRIPTION OF EMBODIMENTS

Overview

Figure 1:
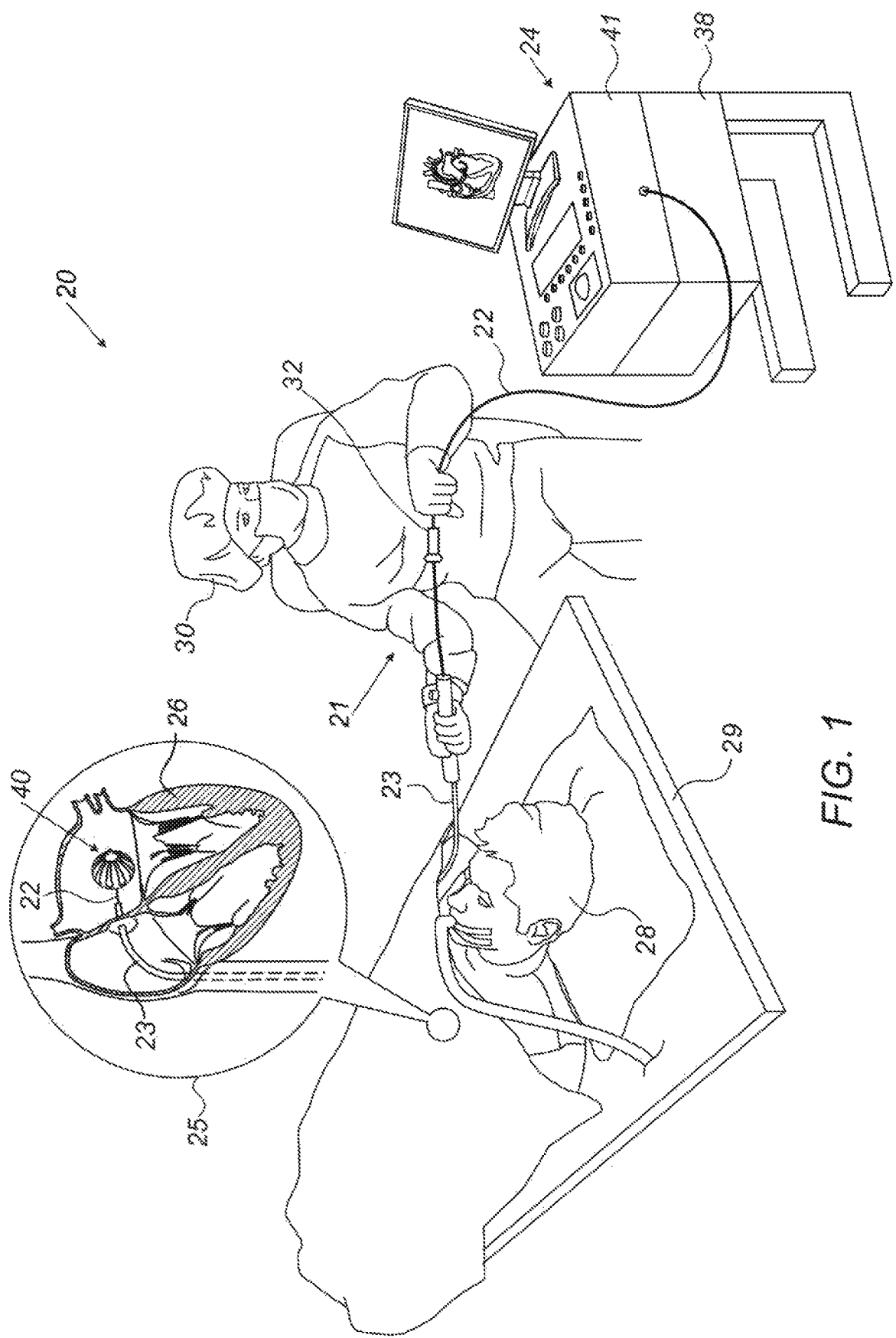
FIG. 1 is a schematic, pictorial illustration of a balloon catheterization system comprising a telescopic balloon assembly, in accordance with an embodiment of the present invention.

Embodiments of the present invention that are described hereinafter provide improved methods and mechanisms for expanding and collapsing a balloon at a distal end of a medical instrument, e.g., a cardiac ablation catheter. In some embodiments, the medical instrument comprises a telescopic assembly fitted at a distal end of a shaft, an elastic element coupled to retain the telescopic assembly in an elongated state, a puller-wire connected to compress the telescopic assembly under control of a physician. An inflatable balloon is coupled to be retained in an elongated, collapsed state by the telescopic assembly being in an elongated state, and to be prepared for inflation and expand due to the telescopic assembly being compressed.

The puller-wire may be thin and highly flexible (e.g., as there is no need for the wire to be stiff as for example pusher-wires need to). The puller-wire is connected to the telescopic assembly such that pulling the puller-wire compresses the telescopic assembly. The elastic element, such as a spring, is coupled to the telescopic assembly such that when it self-elongates it elongates the telescopic assembly. In some embodiments, an inflatable balloon is coupled to the telescopic assembly such that the compression of the telescopic assembly facilitates the inflation of the balloon, while elongating the telescopic assembly assists collapsing the balloon.

The compression and extension of the telescopic assembly may be realized by causing one or more sections of the telescopic assembly to telescopically slide into one another. Various realizations and variations of a telescopic motion that compresses the telescopic assembly by pulling a puller-wire, and elongating the telescopic assembly by a self-elongating elastic element applying an opposing force, are possible.

As an example, the telescopic assembly may by compressed by puling proximally a distal section, or by pulling distally a proximal section, or by a combination thereof, depending on detailed alternative designs of elements such as transmission mechanisms of the puller-wire and arrangements of one or more opposing elastic elements. Hence, embodiments that are provided hereinafter serve to exemplify several possible realizations, whereas potentially many more may occur to persons skilled in the art.

In various embodiment, any relevant implementation of (a) a telescopic assembly (b) an elastic element, and (c) a puller-wire, which together enable the elongation and compression of the telescopic assembly as describes herein. It is therefore to be understood that certain mechanical parts and/or principles may be included or omitted in possible realizations, and that the principles provided by the disclosed embodiments can be implemented using numerous other possible realizations.

In some embodiments, the telescopic assembly includes a movable distal section and a proximal section fixed to a shaft. The telescopic motion between the distal section and the fixed proximal section either compresses or elongates the overall length of the two-section telescopic assembly.

In some embodiments an inflated balloon is coupled to the telescopic assembly. A distal end of the inflated balloon is coupled to the distal end of the distal section, while a proximal end of the balloon is coupled to the proximal end of the proximal section. With this configuration, motion of the distal section in the distal direction, which elongates the telescopic assembly, elongates the balloon so as to assist its collapsing by evacuating the saline from the interior of the balloon. By the same token, motion of the distal section in the proximal direction, which compresses the telescopic assembly, contracts the balloon in a longitudinal direction (i.e., parallel to the telescopic motion) and by doing so allows the balloon to be inflated.

In some embodiments, the elastic element retains the telescopic assembly in a normally-elongated state. A puller-wire running through the shaft is connected to the distal section. When the puller-wire is pulled in the proximal direction by the physician, the puller-wire pulls the distal section proximally so as to compress the telescopic assembly. The compression of the telescopic assembly contracts the balloon from its elongated state and thus expands the balloon to make room for inflating the balloon (e.g., by filling the balloon with saline solution), in preparation of performing some diagnostics and/or a therapy.

In some embodiments, the elastic element comprises one or more self-elongating splines or springs, which elongate the telescopic assembly. In some embodiments, the one or more splines or springs are fixed at their proximal ends to the proximal section and are fixed at their distal ends to the distal section. The splines or springs have a preformed shape that is an elongated one. As a result of their induced inherent tendency to self-elongate, the splines or springs force the distal section of the telescopic assembly to move distally so as to elongate the telescopic assembly to its maximal designed length. In order for the elongation to occur, the pulling force by which the puller-wire is pulled or held should be weaker than the force that the splines or springs exert on the distal section. The inflatable balloon coupled to the telescopic assembly will be correspondingly elongated (and thus the telescopic assembly assists in bringing the balloon to a collapsed state).

Once the physician decides to retract the balloon assembly, he or she releases some or all of the pulling tension in the puller-wire. The splines then self-elongate and push the distal section distally to assist the balloon in collapsing. When the balloon is collapsed and fully elongated, the physician can safely retract the balloon assembly into the catheter sheath and maneuver the catheter out of the patient's body.

When using the disclosed configurations, the puller-wire may be very thin and highly flexible. This feature is in contrast to solutions based on pusher-wire, in which the pusher-wire must be rigid and therefore thick and less flexible. As such, the disclosed techniques, enable highly flexible catheter designs capable of performing sharp turns. A highly flexible balloon catheter using the disclosed telescopic assembly assisted by a puller-wire may thus particularly maneuverable via sharp deflections of blood vessels, and by so overcoming an obstacle that may otherwise hinder catheterization. Moreover, the overall catheter diameter may be reduced.

System Description

FIG. 1 is a schematic, pictorial illustration of a balloon catheterization system 20 comprising a telescopic balloon assembly 40, in accordance with an embodiment of the present invention. System 20 comprises a catheter 21, wherein, as an inset 25 shows, a distal end of shaft 22 of the catheter is inserted through a sheath 23 into a heart 26 of a patient 28 lying on a table 29. The proximal end of catheter 21 is connected to a control console 24. In the embodiment described herein, catheter 21 may be used for any suitable therapeutic and/or diagnostic purposes, such as electrical sensing, balloon angioplasty and ablation of tissue in heart 26, to name just few possible medical usages of inflatable balloon catheters.

Physician 30 navigates the distal end of shaft 22 to a target location in heart 26 by manipulating shaft 22 using a manipulator 32 near the proximal end of the catheter and/or deflection from the sheath 23. During the insertion of shaft 22, telescopic balloon assembly 40 is maintained in a collapsed configuration by sheath 23. By containing telescopic balloon assembly 40 in an elongated (and thus collapsed) configuration, sheath 23 also serves to minimize vascular trauma along the way to target location.

Control console 24 comprises a processor 41, typically a general-purpose computer, with suitable front end and interface circuits 38 for receiving signals from catheter 21, as well as for applying treatment via catheter 21 in heart 26 and for controlling the other components of system 20. Processor 41 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise other components and perform non-cardiac treatments.

Balloon Catheter Assisted by Pulling a Puller-Wire

Figure 2A:
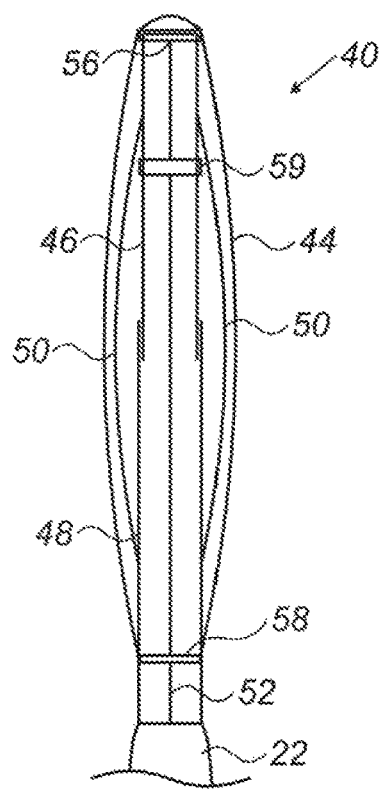
FIGS. 2A and 2B are schematic, pictorial illustrations of a telescopic balloon assembly in telescopically elongated and compressed states, in accordance with an embodiment of the present invention.
Figure 2B:
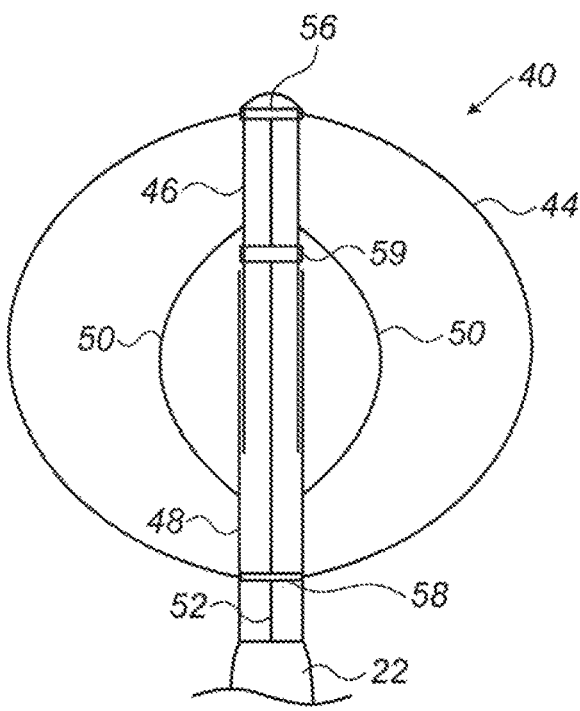

FIGS. 2A and 2B are schematic, pictorial illustrations of telescopic balloon assembly 40 in elongated and compressed states, in accordance with an embodiment of the present invention.

FIG. 2A show telescopic balloon assembly 40 in an elongated state fitted at the distal end of shaft 22. As seen, a proximal section 48 and a distal section 46 are assembled into a two-part structure of telescopic assembly 40. In some embodiments proximal section 48 and a distal section 46 comprise a tube, but many other, non-cylindrical cross-sections, may be used. Proximal section 48 is coupled to shaft 22, while distal section 46 can move telescopically inside proximal section 48, i.e., its motion is either proximally or distally along a direction parallel to shaft 22. As seen, balloon 44 is coupled at its distal end to distal section 46 by an anchor 56 and is coupled at its proximal end to proximal section 48 by an anchor 58.

The elongation of telescopic balloon assembly 40 is caused by splines 50 self-elongating towards their pre-shaped lengths. As seen, inflatable balloon 44 is retained in an elongated state by telescopic assembly 40 being in an elongated state.

A puller-wire 52 runs through shaft 22 and within the two-part telescopic assembly and is connected to distal section 46 at a distal edge of section 46. In an embodiment, puller-wire 52 is operated (e.g., pulled or relaxed) from a handle of catheter 21. When physician 30 is ready to inflate balloon 44, the physician command compressing telescopic balloon assembly 40, which is performed by pulling of puller-wire 52. As seen in FIG. 2B, the two-part telescopic assembly 40 is compressed by pulling puller-wire 52 proximally forcefully enough for distal section 46 to force one or more elastic splines 50 to bend. In an embodiment, a stopper 59 limits the motion of distal section 46 to the required length. As seen in FIG. 2B, balloon 44 is longitudinally contracted and so as to being ready to be inflated, for example, by pressurized saline solution.

When the physician command the elongation of telescopic balloon assembly 40, the force at which puller-wire 52 is pulled proximally is reduced sufficiently by a pulling apparatus (not described) to let splines 50 to self-elongate. Correspondingly, inflatable balloon 44 is elongated, making the balloon ready for retraction into sheath 23.

The example illustrations shown in FIGS. 2A and 2B are chosen purely for the sake of conceptual clarity. Elastic splines 50 may have different shapes and may be made from various materials. Other telescopic arrangements are possible. For example, distal section 46 may encompass proximal section 48 from the outside. As another example, the telescopic assembly may comprise more than two sections. Stopper 59 is brought by way of example only, the limit over distal section 46 motion may be realized, among other options, electronically, by using for example, a proximity sensor. As another example, the limit over of the motion of distal section 46 can be realized by setting the pulling force (transmitted by puller-wire 52) such it is balanced by the resistance elastic splines 50 at a given bend of splines 50, which brings the telescopic assembly into static equilibrium at a given pre-designed length.

Figure 3A:
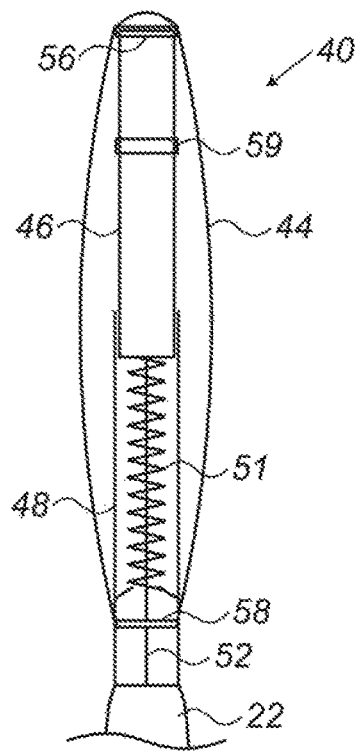
FIGS. 3A and 3B are schematic, pictorial illustrations of a telescopic balloon assembly in telescopically elongated and compressed states, in accordance with another embodiment of the present invention.
Figure 3B:
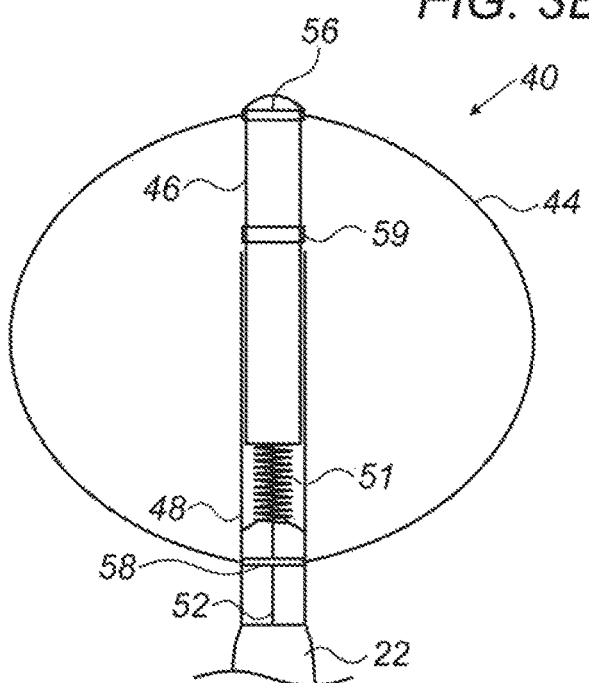

FIGS. 3A and 3B are schematic, pictorial illustrations of telescopic balloon assembly 40 in elongated and compressed states, in accordance with another embodiment of the present invention.

In the embodiment exemplified by FIGS. 3A and 3B, a spiral (helical) spring 51, which is enclosed in proximal section 48 and pressed against distal section 46, is used for pushing distal section 46 to elongate telescopic balloon assembly 40. As seen in FIG. 3B, pulling puller-wire 52 compresses telescopic balloon assembly 40 and by so longitudinally contracts balloon 44 to enable the inflation of balloon 44. The example illustration shown in FIGS. 3A and 3B is brought mainly to demonstrate that various designs are possible for achieving the same end result elaborated above of compressing and elongating telescopic balloon assembly 40. Additional designs with vast options for of elements and materials may occur to persons skill in the art.

Figure 4:
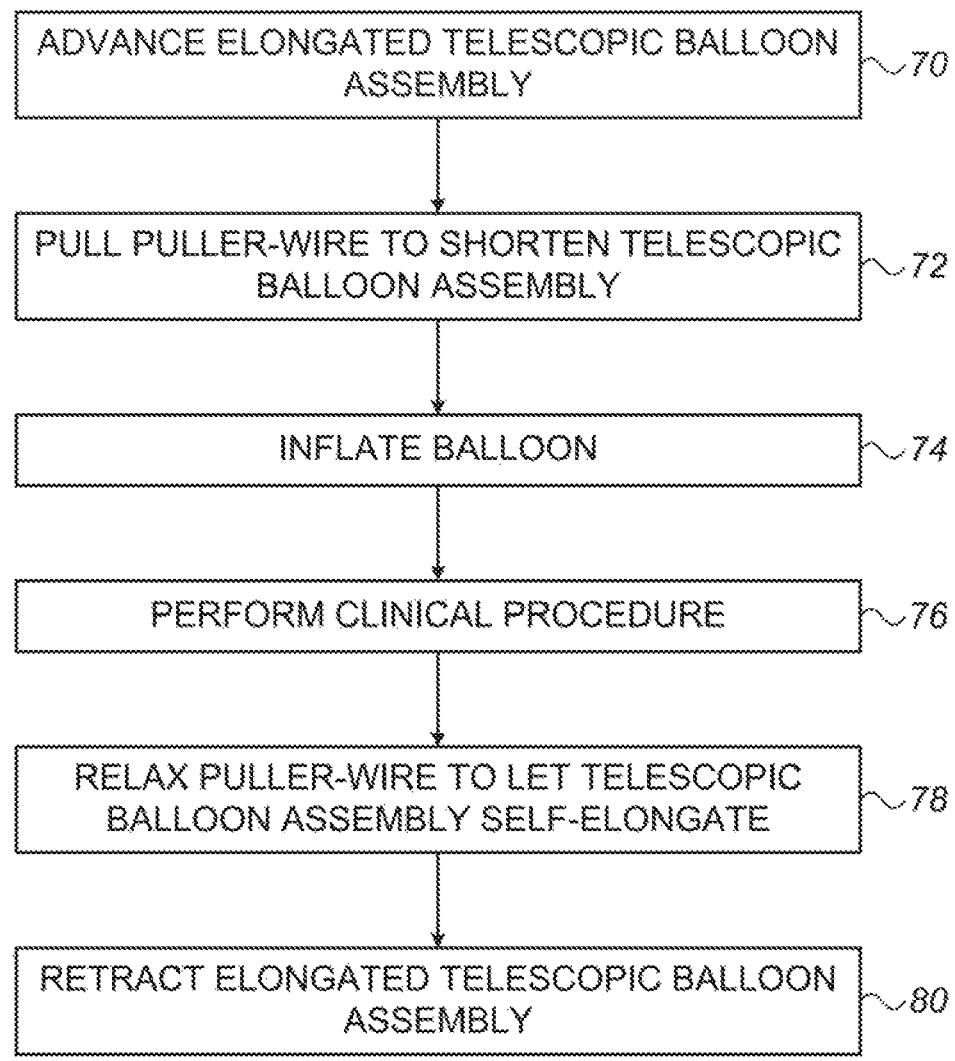
FIG. 4 is a flow-chart that schematically illustrates a method for telescopically compressing and elongating a telescopic balloon assembly using a puller-wire and an elastic element, respectively, in accordance with an embodiment of the present invention.

FIG. 4 is a flow-chart that schematically illustrates a method for telescopically compressing and elongating telescopic balloon assembly 40 using puller-wire 52, in accordance with an embodiment of the present invention.

The process may begin with physician 30 advancing telescopic balloon assembly 40 while being held collapsed in sheath 23, at a balloon advancement step 70. Physician 30 may advance sheath 23 through sharp deflections of blood vessels, as such pose less of an obstacle to the highly flexible shaft 22 of catheter 21 (a flexibility attributed largely to the high flexibility of puller-wire 52 within shaft 22).

After physician 30 navigated telescopic balloon assembly 40 to its target location in heart 26, physician 30 retracts sheath 23 or advances balloon assembly 40, exposing the elongated telescopic balloon assembly 40. Physician 30 then commands the pulling of puller-wire 52, so as to telescopically compress telescopic balloon assembly 40 and by so longitudinally contracting balloon 44 to enable inflating balloon 44, at a pulling step 72. Physician 30 inflates balloon 44, at an inflation step 74, and performs the required clinical procedure, at a clinical step 76.

Once physician 30 wishes to deflate balloon 44, physician 30 commands then a relaxation of tension which puller-wire 52 transmits, allowing splines 50 to self-elongate so as to telescopically elongate telescopic balloon assembly 40 and correspondingly elongate balloon 44, at an elongation step 78. The elongation of balloon 44 assists deflating and collapsing balloon 44. The physician can then safely retract the elongated and collapsed telescopic balloon assembly 40 back into sheath 23, in retraction step 80.

The example flow chart shown in FIG. 4 is chosen purely for the sake of conceptual clarity. The operation method of telescopic balloon assembly 40 is to serve only as an illustrative example of a puller-wire method disclosed. For example, physician 30 may perform additional steps prior, during or after clinical step 74.

Although the embodiments described herein mainly address cardiac applications, the methods and systems described herein can also be used in other applications, such as otolaryngology or neurology procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter comprising:
a shaft for insertion into a body of a patient;
a telescopic assembly including proximal and distal tubular members in a telescopic configuration, the distal tubular member having a distal anchor, the proximal tubular member having a proximal anchor;
an inflatable balloon, which is coupled to a distal anchor of the distal tubular member and the proximal anchor of the proximal tubular member; and
a puller-wire, which runs through the shaft and is connected to the distal anchor so that when the puller wire is pulled proximally, the balloon is shortened along its length.

2. The catheter according to claim 1, further comprising a stopper disposed proximate the distal anchor to limit the motion of the proximal and distal tubular members when the puller wire is pulled.

3. The catheter according to claim 1, further comprising an elastic element coupled to the proximal and distal tubular members to cause the proximal and distal tubular members to elongate.

4. The catheter according to claim 3, wherein the elastic element comprises a coil spring.

5. The catheter according to claim 4, wherein the coil spring is disposed outside of the proximal and distal tubular members.

6. The catheter according to claim 4, wherein the coil spring is disposed inside one of the first or proximal tubular members.

7. The catheter according to claim 1, wherein the elastic element comprises one or more elastic splines, each spline having a first end connected to the distal tubular member and a second end connected to the proximal tubular member.

* * * * *